(12) United States Patent
Renz et al.

(10) Patent No.: US 9,233,205 B2
(45) Date of Patent: Jan. 12, 2016

(54) INJECTION DEVICE HAVING INJECTION VOLUME ADJUSTMENT

(75) Inventors: Andreas Renz, Sulz (DE); Wilfried Weber, Schopfloch (DE)

(73) Assignee: DIETER HÖLZE TECHNIK-PROJEKTE GMBH, Deckenpfronn (DE)

( * ) Notice: Subject to any disclaimer, the term of this patent is extended or adjusted under 35 U.S.C. 154(b) by 1148 days.

(21) Appl. No.: 13/254,919

(22) PCT Filed: Jan. 22, 2010

(86) PCT No.: PCT/EP2010/000373
§ 371 (c)(1),
(2), (4) Date: Nov. 21, 2011

(87) PCT Pub. No.: WO2010/099850
PCT Pub. Date: Sep. 10, 2010

(65) Prior Publication Data
US 2012/0056019 A1    Mar. 8, 2012

(30) Foreign Application Priority Data
Mar. 3, 2009   (DE) .................... 20 2009 003 009 U

(51) Int. Cl.
*A61M 5/20* (2006.01)
*A61M 5/24* (2006.01)
*A61M 5/315* (2006.01)
*A61M 5/46* (2006.01)

(52) U.S. Cl.
CPC .............. *A61M 5/2033* (2013.01); *A61M 5/24* (2013.01); *A61M 5/31546* (2013.01); *A61M 5/31553* (2013.01); *A61M 5/31563* (2013.01); *A61M 5/31573* (2013.01); *A61M 5/31591* (2013.01); *A61M 5/46* (2013.01); *A61M 2005/2006* (2013.01); *A61M 2005/206* (2013.01); *A61M 2005/2414* (2013.01)

(58) Field of Classification Search
CPC .................... A61M 5/31591; A61M 5/31573; A61M 5/31546; A61M 5/31563; A61M 5/31553; A61M 2005/2006; A61M 2005/206; A61M 2005/2414; A61M 5/46; A61M 5/24
USPC ........... 604/131, 134, 82, 117, 135, 136, 110, 604/154, 156, 157, 208; 128/DIG. 3, 128/DIG. 13, DIG. 1
See application file for complete search history.

(56) References Cited

U.S. PATENT DOCUMENTS 3,702,609 A    11/1972   Steiner
4,194,505 A     3/1980   Schmitz
(Continued)

FOREIGN PATENT DOCUMENTS

EP         1690559 A1      8/2006
WO      WO 9828029 A1      7/1998
WO   WO 2007033638 A1      3/2007

*Primary Examiner* — Kami A Bosworth
*Assistant Examiner* — Hamza Darb
(74) *Attorney, Agent, or Firm* — Browdy and Neimark, P.L.L.C.

(57) ABSTRACT

An injection device (2) comprises a housing (4) in which a receiving chamber (6) is provided for an injection mechanism (8) having an injection fluid container (10) that can be pressed out by means of an injection plunger (12). The injection device (2) further comprises an actuating device (18) that can be driven for automatically pressing out the injection fluid container (10), wherein said actuating device can be displaced between an insertion/removal position outside of the receiving chamber (6) and an injection position within the receiving chamber (6), wherein the actuating device (18) is spaced by a release distance (d) from the receiving chamber (6) in the insertion/removal position. A contact mechanism (22) is provided, by means of which the actuating device (18) can be brought into a stop position in which an actuating stop (26) of the actuating device (18) contacts the injection plunger (12) and in which an injection volume adjustment (28) is automatically actuated.

11 Claims, 8 Drawing Sheets

(56) References Cited

U.S. PATENT DOCUMENTS

Figure 1:
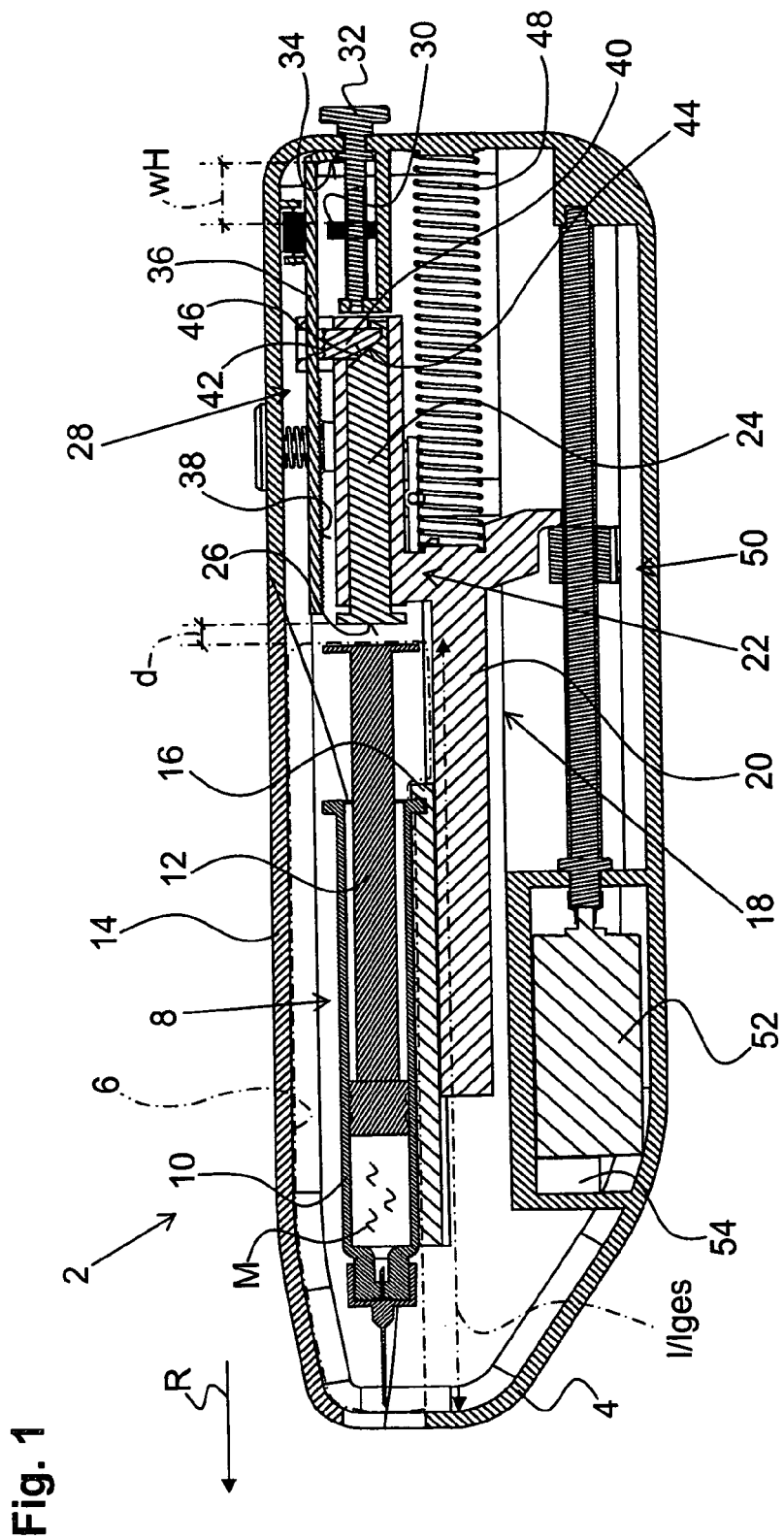

| | | | |
|---|---|---|---|
| 4,518,387 A * | 5/1985 | Murphy et al. | 604/187 |
| 4,668,220 A * | 5/1987 | Hawrylenko | 604/155 |
| 7,678,072 B2 | 3/2010 | Weber | |
| 8,641,669 B2 * | 2/2014 | Renz et al. | 604/136 |
| 2004/0078001 A1 | 4/2004 | Langley et al. | |
| 2004/0176729 A1 * | 9/2004 | Langley et al. | 604/207 |
| 2008/0188798 A1 * | 8/2008 | Weber | 604/82 |

* cited by examiner

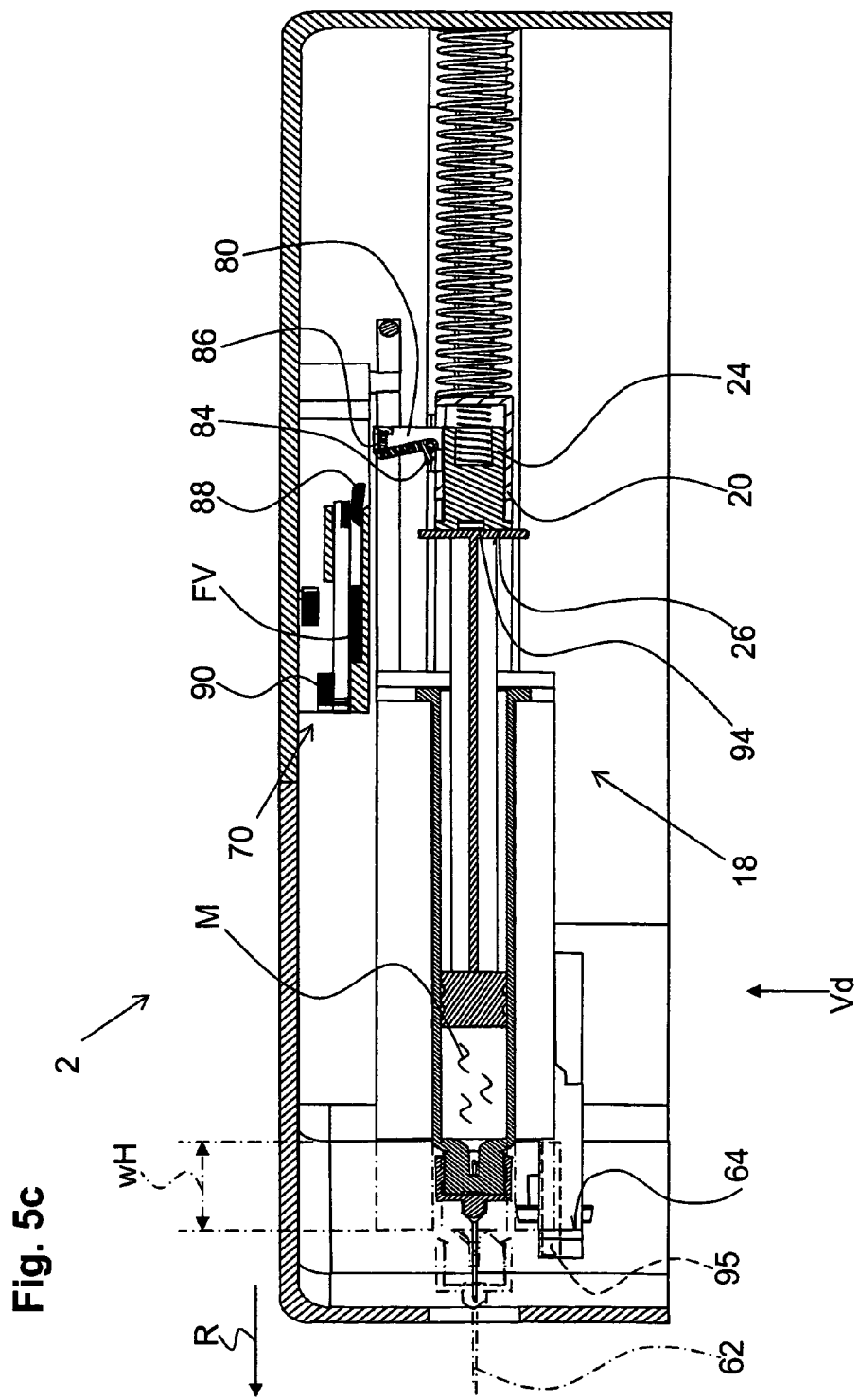

INJECTION DEVICE HAVING INJECTION VOLUME ADJUSTMENT

The invention relates to an injection device for automatically expressing an injection mechanism according to the preamble of claim 1. For this purpose the injection device comprises a housing in which a receiving chamber that is accessible in particular transverse to an injection direction is provided for an injection mechanism to be inserted that has an injection fluid container that can be expressed by means of an injection plunger. The injection device further comprises an actuating device for automatically expressing the injection fluid container, which actuating device can be displaced between an insertion/removal position outside the receiving chamber and an injection position within the receiving chamber. The actuating device is spaced by a release distance from the receiving chamber in the insertion/removal position, thereby facilitating the insertion or removal of the injection device.

From WO 2007/033638 there is known an injection device for receiving and actuating a two-chamber ampoule. Same has a plunger for actuating the ampoule, the plunger being held in the initial position thereof spaced at a distance from an ampoule plunger, in order to enable the two-chamber ampoule to be inserted and removed without difficulty. The injection device, upon activation thereof, performs a mixing stroke during which the plunger is automatically moved into contact with the ampoule plunger and displaces same.

For various applications it is desirable or necessary to inject a relatively precise amount of the particular medication. However, even with preportioned medication dosages, and in particular with freshly drawn-up syringes, certain tolerances do occur in terms of the amount of medication taken up in each case.

For this reason there exists a need, even with a self-operating injection device, to be able to adjust the injection volume relatively exactly that will be injected during an impending application, independently from the amount of medication taken up in the injection device. On the other hand, however, the particular injection mechanism should also be easy and quick to insert into the injection device and to remove therefrom after use.

It is therefore the aim of the invention to make an exact injection volume adjustment and user-friendly operation possible in an injection device of the generic type.

This aim is achieved by an injection device having the features of claim 1. In this injection device a contact mechanism is provided, by means of which the actuating device can be brought into a stop position. In this stop position an actuating stop of the actuating device contacts the injection plunger of the injection mechanism accommodated in the actuating device, free of play. At the same time an injection volume adjustment is automatically actuated or activated exactly in this stop position. The injection volume adjustment is formed by a mechanical or by an electrically or electronically controlled means that is suitable for a predefined presetting of a fixed or adjustable injection volume of the medium to be injected. In this way it is possible to bring the actuating device into contact with the injection plunger, and at the same time define a zero position for the injection volume adjustment which is independent of potential production tolerances and/or of the amount of medication taken up. Starting from this zero position an exact stroke distance can thus be set that corresponds to a predefined injection volume of the particular medication to be injected.

The injection volume adjustment advantageously limits, starting from the stop position, a stroke distance of the actuating device along an injection direction. This enables a simple but precise setting of the plunger distance and, hence, of the injection volume to be administered.

In a particularly preferred embodiment the actuating stop is held movable on the remaining actuating device and the contact mechanism has fixing means whereby the actuating stop can be fixed in place on the remaining actuating device according to the position of the injection plunger. This makes it possible to ensure a stop position of the actuating device that is free of play, regardless of potential production tolerances of the injection device.

Additionally, it is advantageous when the injection volume adjustment is actuated via the contact mechanism, such that same, in addition to displacing the actuating stop and locking same on the actuating device, at the same time also serves for activating the injection volume adjustment. In this way the activation of the injection volume adjustment simultaneously with the stop position being reached can be achieved in a particularly simple way.

Furthermore, it is advantageous when the actuating stop is formed by an actuating plunger capable of being displaced on the actuating device in the injection direction, and the fixing means create a form closure on contact of the actuating stop with the injection plunger which form closure acts opposite to the injection direction, whereby a positionally stable fixing of the actuating stop on the remaining actuating device during application of a force upon the injection plunger can be ensured.

In a particularly advantageous embodiment, the contact mechanism is capable of being activated or deactivated according to the position of a cover of the housing. In this way it can be ensured that the actuating device is not inadvertently activated when the cover is open.

The contact mechanism advantageously has an actuating member capable of being displaced through the cover that assumes a blocking position when the cover is open in which blocking position it holds the fixing means and the actuating plunger against a respective bias in the insertion/removal position. In the insertion/removal position, the actuating plunger is arranged in a rear stop position and the locking means are released. This ensures that the full release distance is available, so as to permit a user-friendly insertion or removal of the injection mechanism.

In a further advantageous embodiment, the contact mechanism has a clamping element that is capable of being displaced transverse to the injection direction. This clamping element is displaced into an end position by means of an incline by the actuating plunger when same is in contact with the injection plunger, in which end position it blocks a movement of the actuating plunger opposite to the injection direction with respect to the remaining actuating device. At the same time the actuating plunger is fixed in place on a movable stop element of the injection volume adjustment. In this manner the actuating device is mechanically coupled in the contact position to the injection volume adjustment, in order to be able to limit the stroke distance thereof in a simple manner.

It is advantageous when the movable stop element has a toothing with which a mating toothing of the coupling element can be brought into engagement, in order to achieve a solid form closure between the actuating device and the movable stop element.

Furthermore, it is advantageous when the injection volume adjustment has an adjustable end stop that is arranged in the direction of movement of the movable stop element. In this way the stroke distance and, hence, the injection volume to be administered can be adjusted or changed as needed.

The end stop is advantageously displaceable via a set screw that is accessible from outside the housing, in order to allow the adjustable injection volume adjustment to be made available particularly cost-effectively.

In a further advantageous embodiment the injection volume adjustment is formed by a control unit of an electric motor. The control unit is capable of being actuated by means of the signal of a sensor with which the stop position of the actuating device can be detected. In this way a particularly precise and variable injection volume adjustment is possible starting from the stop position.

It is advantageous in this context when the injection volume adjustment has a counting function whereby a number of completed revolutions of the motor starting from the stop position can be set. In this way a required number of revolutions by means of which the transport mechanism is moved into an end stop position can be calculated and set via the injection volume adjustment, the spacing of the end stop position from the stop position corresponding to the stroke distance that the injection slide must travel with regard to the injection mechanism used, in order to first perform the pricking stroke and then express the volume of medication to be injected set on the injection volume adjustment. It is also possible to provide for and set varyingly long injection strokes via the control unit for differently dimensioned injection mechanisms or for different injection applications.

Figure 2A:
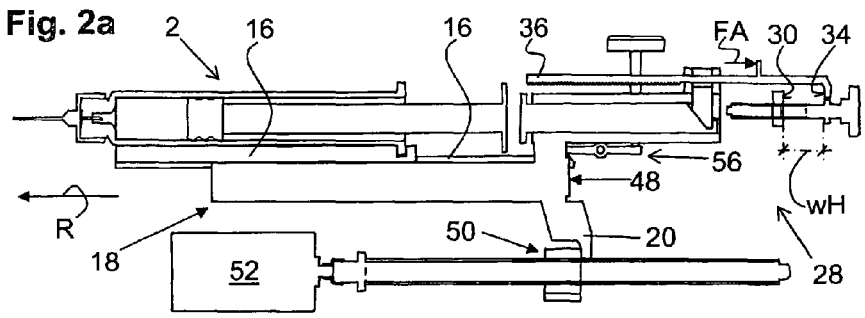
Figure 2B:
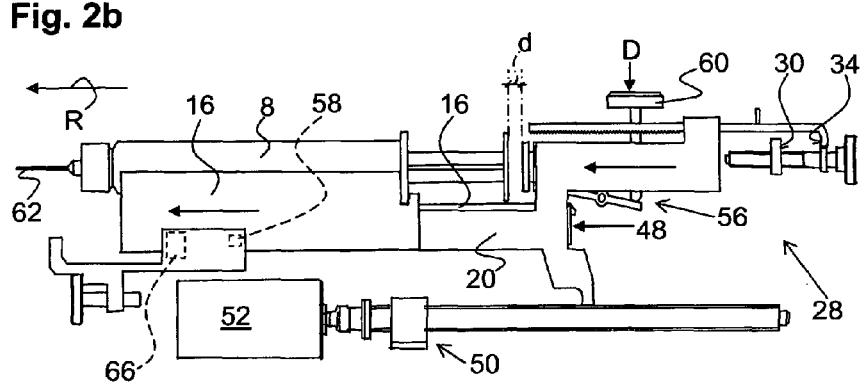
Figure 2C:
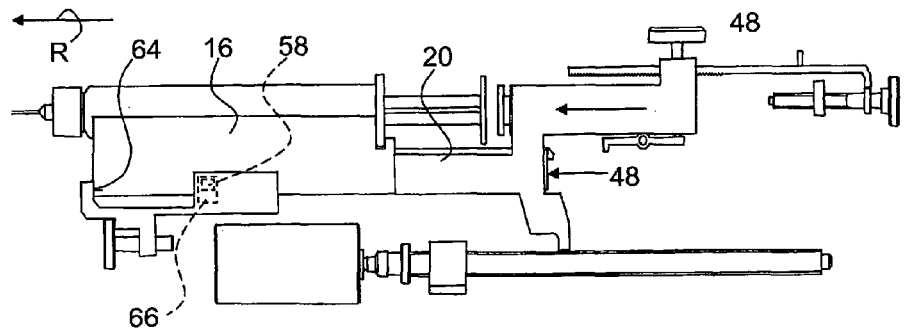
Figure 2D:
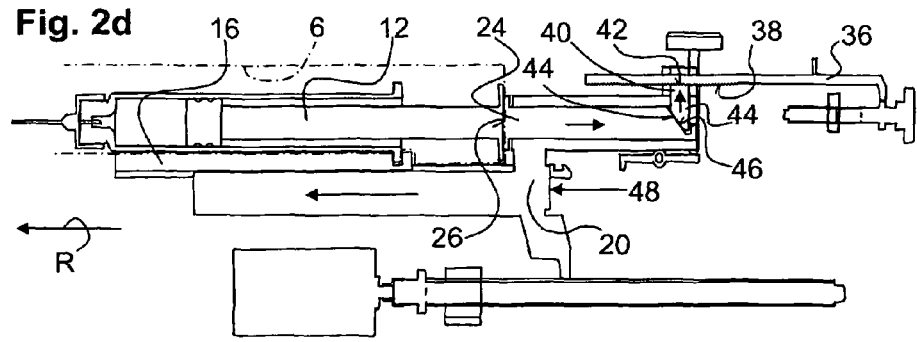
Figure 2E:
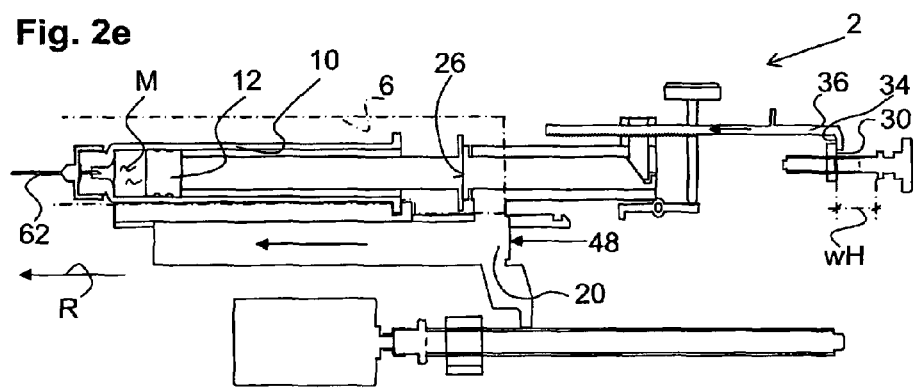
Figure 2F:
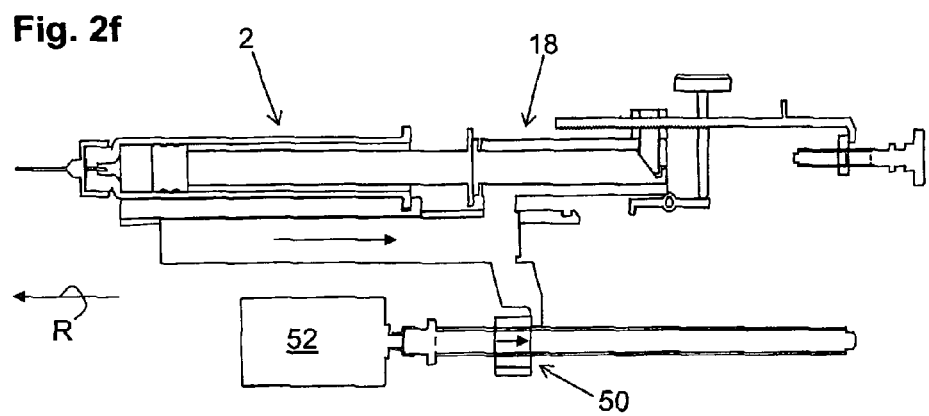
Figure 3:
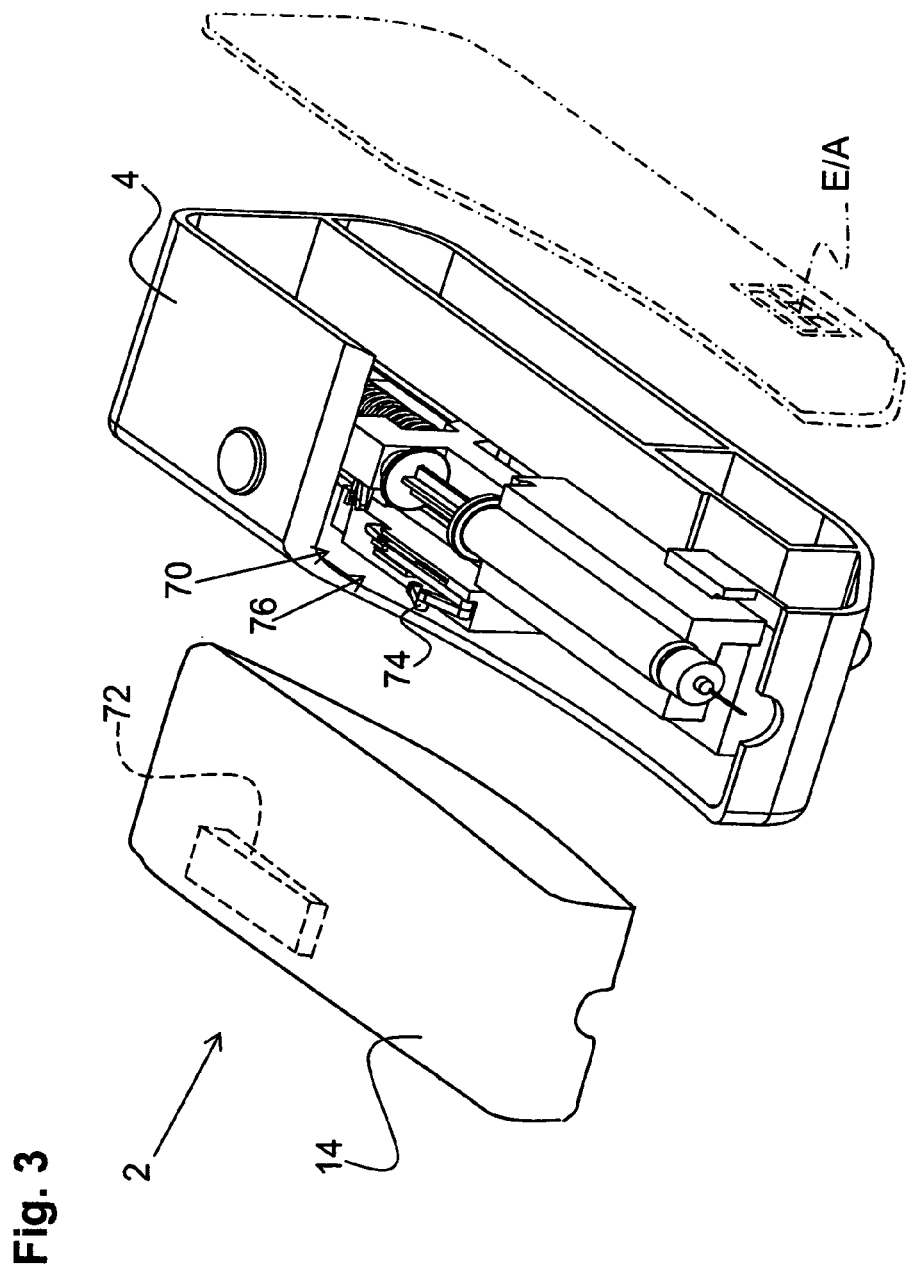
Figure 4:
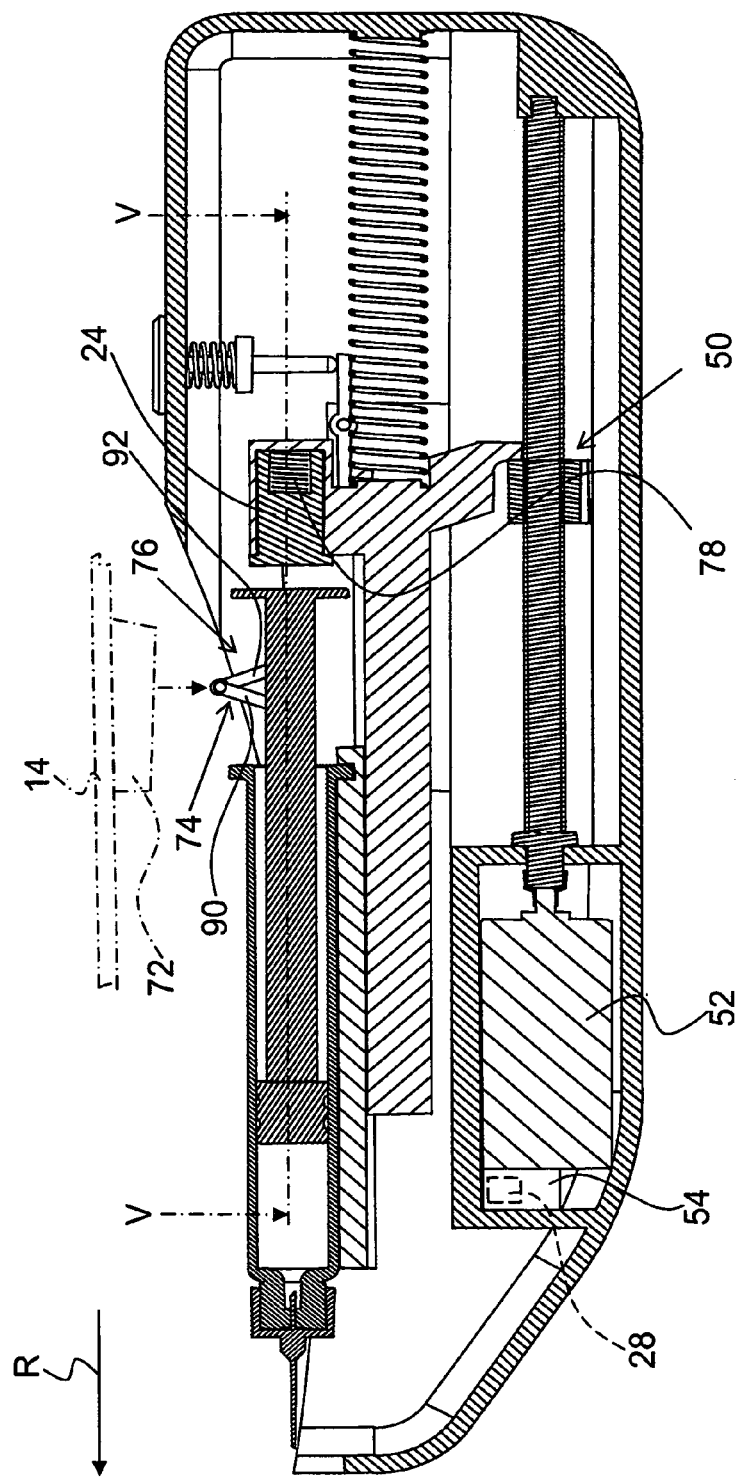
Figure 5A:
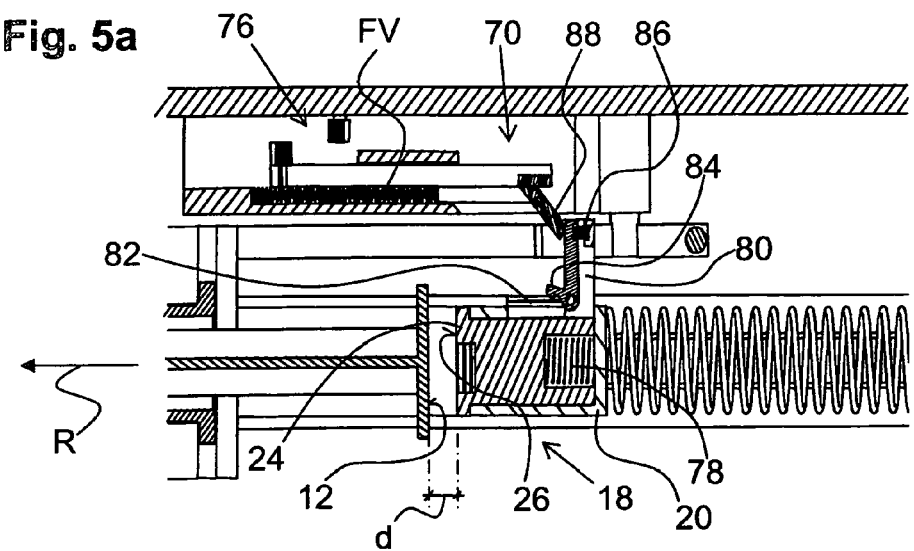
Figure 5B:
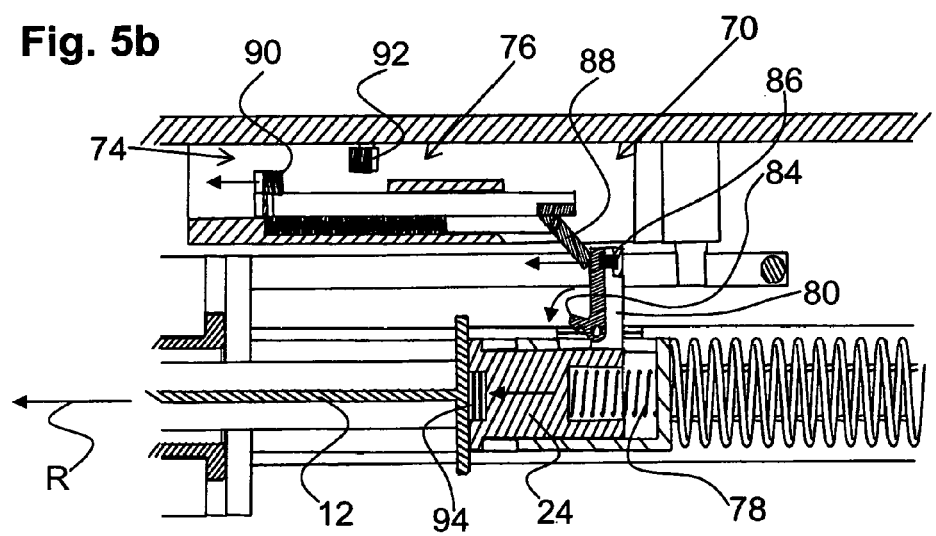
Figure 5D:
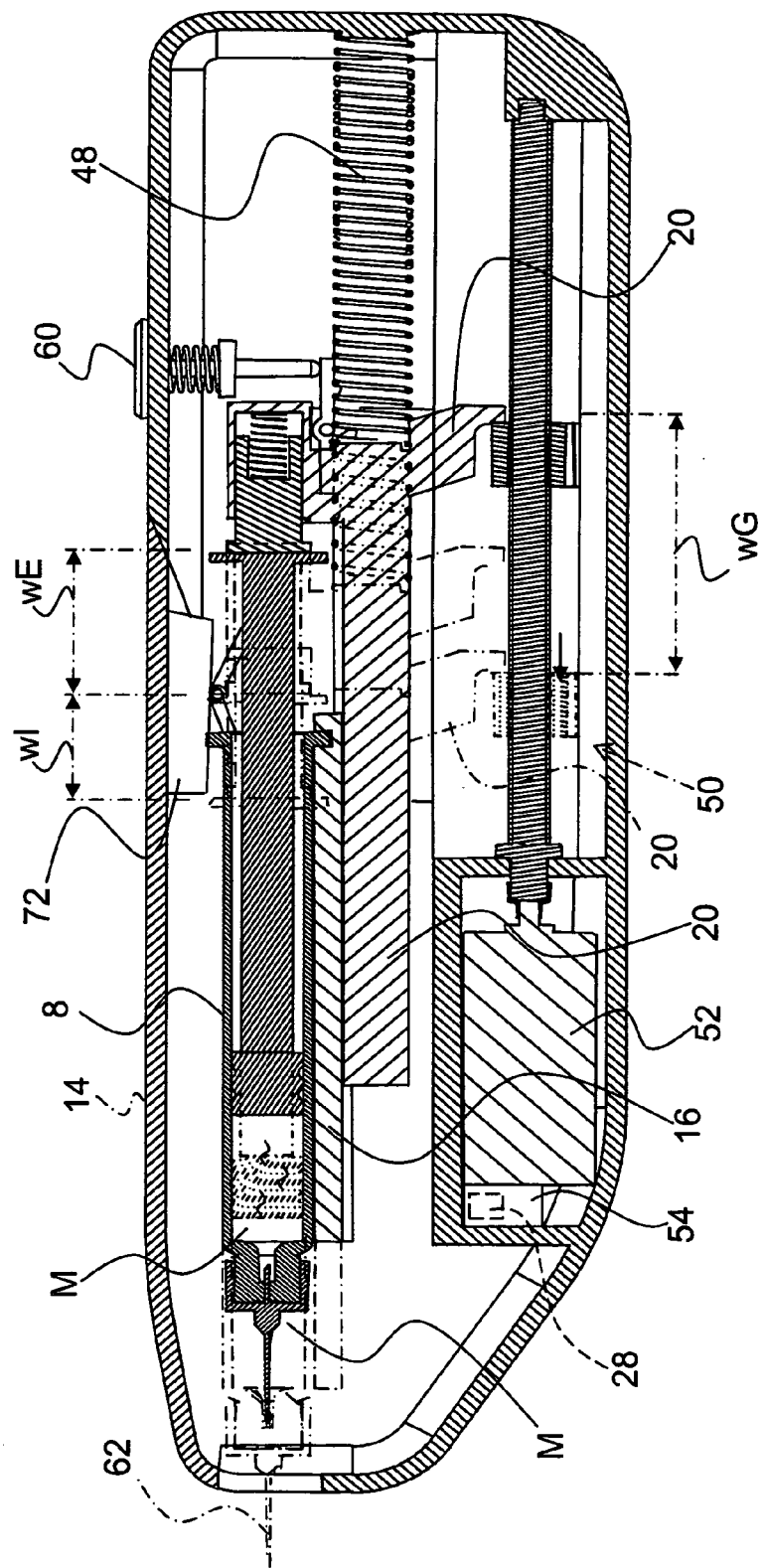

An embodiment of the invention is shown in the figures, in which:

FIG. 1 shows a longitudinal section of an injection device according to the invention, FIG. 2a shows a simplified sectional illustration of the injection device according to FIG. 1 in an initial position, in which an actuating device is situated in an insertion/removal position, FIG. 2b shows an illustration of the injection device during actuation of a start button, FIG. 2c shows an illustration of the injection device on reaching a predefined pricking depth, FIG. 2d shows an illustration of the actuating device in a stop position, FIG. 2e shows an illustration of the actuating device in an injection position, FIG. 2f shows an illustration of the injection device at the beginning of a return stroke, FIG. 3 shows a perspective view of the injection device having an alternative embodiment of a contact mechanism, FIG. 4 shows a longitudinal section through the injection device according to FIG. 3 in the initial position, with an open cover, FIG. 5a shows a section through the contact mechanism in plane V-V of FIG. 4, FIG. 5b shows a section through the contact mechanism during closing of a cover, FIG. 5c shows a section through the contact mechanism with the cover fully closed, and FIG. 5d shows a sectional view of the injection device in the direction Vd of FIG. 5c.

FIG. 1 shows an injection device 2 according to the invention, comprising a housing 4. The housing 4 forms a receiving chamber 6 for a syringe-shaped injection mechanism 8 that has an injection fluid container 10. The injection fluid container 10 serves to receive a medication M to be injected and is capable of being expressed by means of an injection plunger 12.

In order to accommodate the injection mechanism 8, the receiving chamber 6 has a virtual longitudinal extension 1 that corresponds to at least a total length 1 ges of the injection mechanism 8 intended to be used on the injection device 2, with an intended maximum volume of taken up medication M.

In order to insert or remove the injection mechanism 8, the housing 4 has a removable cover 14 that has, with respect to an injection direction R, a lateral access to the receiving chamber 6, thereby permitting lateral insertion or removal of the injection mechanism. During insertion, the injection mechanism is fixed in place on a pricking slide 16 of an actuating device 18. The latter further has an injection slide 20 that serves to act upon the injection plunger 12 and is capable of being moved relative to the pricking slide 16 for this purpose.

A contact mechanism, identified as a whole by reference numeral 22, is provided on the injection slide 20. This contact mechanism has an actuating plunger 24 that is movably supported on the injection slide 20 and that forms at the end thereof situated in the injection direction R an actuating stop 26. This actuating stop 26 serves for contacting the injection plunger 12.

In order to permit unimpeded insertion and removal of the injection mechanism 8, the actuating device 18 is moved in the initial position shown of the injection device 2 into an insertion/removal position in which the actuating stop 26 is spaced by a release distance d from the receiving chamber 6 or from the injection plunger 12 of the injection mechanism 8, which is shown already inserted. This serves to prevent in particular a tilting of the injection mechanism 8 during the insertion or removal.

Furthermore, an injection volume adjustment 28 is provided between the injection slide 20 and the housing 4. This injection volume adjustment has an end stop 30 that is capable of being displaced parallel to the injection direction R via a set screw 32 that is accessible from outside the housing 4. This end stop 30 serves to limit a stroke distance wH of a movable stop 34 that is formed on a stop element 36. The latter is supported on the housing 4 so as to be movable parallel to the injection direction R and has a toothing 38 on a side near the injection slide 20.

The stop element 36 is capable of being coupled by means of a coupling element 40 to the injection slide 20 which includes for this purpose a mating toothing 42 that can be brought into engagement with the toothing 38. The coupling element 40 in this arrangement is held on the injection slide 20 so as to be movable transverse to the injection direction R on the injection slide 20 and contacts with a slanted end surface 44 a slanted control surface 46 of the actuating plunger 24, the slanted control surface being formed on an end further away from the actuating stop 26.

As can further be seen from FIG. 1, the injection device 2 has, in order to automatically drive the actuating device 18, a compression spring 48 acting upon the injection slide 20 in the injection direction R. Additionally, an electric transport mechanism 50 that is driven via a motor 52 can be placed against the injection slide 20 opposite to the injection direction R. The transport mechanism 50 can serve both for controlling the speed of the actuating device 18 in the injection direction R and also for returning the actuating device 18 to the initial position following a completed injection process. Provided on the motor 52 is an electric or electronic control unit 54 that includes, for example, a counting member for determining a completed number of revolutions of the motor 52.

The simplified sectional views of FIGS. 2a to 2f show the general configuration of the parts of the injection device 2 that are essential for the invention, during the performance of an injection application.

FIG. 2a shows the initial position of the injection device 2 according to FIG. 1. In this initial position the actuating device 18 is held in the insertion/removal position thereof, the pricking slide 16 being held via a locking mechanism 56 and the injection slide 20 being held by means of the transport mechanism 50 each in a rear end position with respect to the injection direction R. Furthermore, the movable stop element 36 is biased by the force of a spring FA into a rear end position in which the stop 34 has a maximum spacing from the end stop 30 that corresponds to the stroke distance wH set on the injection volume adjustment 28 and to the injection volume defined thereby.

By switching on the motor 52, the transport mechanism is moved, as shown in FIG. 2b, into a position in which it no longer acts upon the injection slide 20. In the position shown, the injection slide is motion coupled by means of a driver 58, which is shown only outlined, to the pricking slide 16 and therefore initially continues to be held in the position thereof. By applying a pressure D onto a start button 60 of the locking mechanism 56 both slides 16, 20 can now be released, such that same are displaced in the injection direction R as a result of the spring force of the compression spring 48 and, as a result, perform a pricking stroke during which a needle 62 of the injection mechanism 8 emerges (not shown) from the housing 4. The release distance d and also the maximum spacing between the end stop 30 and the movable stop 34 set on the injection volume adjustment 28 remains intact during this pricking stroke.

The pricking stroke ends, as shown in FIG. 2c, via contact of the pricking slide 16 with a pricking depth stop 64 provided on the housing. At the same time the motion coupling of the slides 16, 20 via the driver 58 is released by means of appropriate control means 66, such that the injection slide 20 can now be moved further into the injection direction R even relative to the pricking slide 16. The driver 58 and the control means 66, which are also shown only outlined, may be formed for this purpose for example by a sliding block that is mounted on the pricking slide 16 and by control surfaces on the injection slide 20 or on the housing 4 (not shown) that cooperate with said sliding block.

Owing to the relative movement of the injection slide 20 with respect to the pricking slide 16 the actuating stop 26 is now, as shown in FIG. 2d, moved into a stop position in which it is positioned directly against the receiving chamber 6 or contacts the injection plunger 12. Owing to the resistance by the injection plunger 12 the actuating plunger 24 is displaced rearwards in the process on the injection slide 20 opposite to the injection direction R. Owing to this relative movement with respect to the injection slide 20 the slanted control surface 46 presses against the slanted end surface 44 of the coupling element 40 which is thereby displaced toward the stop element 36. In the process, the toothing 38 moves into engagement with the mating toothing 42 which, in turn, effects a motion coupling of the stop element 36 to the injection slide 20. At the same time the coupling element 40 in this engagement position blocks any further displacement of the actuating plunger 24 and thus functions as a fixing means whereby the actuating stop 26 is fixed in place on the injection slide 20 with respect to the injection direction R in a form-closed manner.

During the continued movement of the injection slide 20 due to the action of the compression spring 48 an injection stroke is now performed, during which the actuating stop 26 is moved into an injection position within the receiving chamber 6 and the injection plunger 12 as a result is displaced within the injection fluid container 10. In the process the injection volume of the medication M specified via the injection volume adjustment 28 exits via the needle 62 until the stop element 36 that is moved along by the injection slide 20 in the injection direction R has traveled the length of the stroke distance wH and comes to a stop at the end stop 30, as shown in FIG. 2e. By this contact of the movable stop 34 against the end stop 30 the injection stroke is complete.

In this position according to FIG. 2e the injection device 2 can then dwell for a specified dwelling time, in order to ensure that the set injection volume of the medication M can exit completely through the needle 62.

After the end of the dwelling time, the motor 52 can then, as shown in FIG. 2f, drive the transport mechanism 50 opposite to the injection direction R, in order to move the actuating device 18 back into the insertion/removal position via same and thereby displace the injection device 2 as a whole back into the initial position according to FIG. 2a.

FIG. 3 shows an alternative embodiment of the injection device 2, in which only the contact mechanism 70 provided differs from the embodiment according to FIGS. 1 and 2 while the remaining mode of functioning remains the same. Identical elements of the two embodiments therefore are identified by the same reference signs as in FIGS. 1 and 2.

The contact mechanism 70 of the embodiment according to FIG. 3 differs from the above-described contact mechanism 22 substantially in that same is capable of being actuated according to the position of the cover 14 and moves the actuating device into the stop position even prior to the pricking stroke. The cover 14 may be, as shown, completely removable from and replaceable on the housing 4 or may alternatively also be articulated on same. In order to actuate the contact mechanism 22 an actuating element 72 is formed on the cover 14. On closing of the cover 14, said actuating element is pushed against a knee lever 74 of a direction change gear unit 76 of the contact mechanism 22, the knee lever protruding for example from the opened housing 4 as shown in FIG. 4.

The mode of functioning of the contact mechanism 70 can be seen from FIGS. 5a to 5c, with FIG. 5a showing the contact mechanism 70 in the initial position according to FIG. 4 in which the actuating device 18 is in the insertion/removal position while forming the release distance d between the injection plunger 12 and the actuating stop 26.

The actuating plunger 24 is biased in this arrangement by a spring 78 in the injection direction R and has a side arm 80 that protrudes from a guide slot 82 of the injection slide 20. On the side arm 80, fixing means with a pivotably held snap-in hook 84 are provided. The snap-in hook 84 is acted upon by a spring 86 biasing same toward a locking position.

In the insertion/removal position shown, both the snap-in hook 84 and the actuating plunger 24 are held against the respective biases thereof in a rear stop position with respect to the injection direction R by a pivot arm 88 of the direction change gear unit 76, the pivot arm functioning as actuating member. In this rear stop position, the snap-in hook is released from the injection slide 20. The direction change gear unit 76 is acted upon for this purpose by a bias spring FV that is greater than the sum of forces of the springs 78 and 86.

FIG. 5b shows the contact mechanism 70 during closing of the cover 14, as outlined in FIG. 4 by dash-and-dot lines. As can be seen from this figure, a movable first member 90 of the knee lever 74 is spread away from a fixed member 92 in the injection direction R by the actuating element 72 pressing onto the knee lever 74 (according to FIG. 4). The first member 90 is connected to the pivot arm 88, such that same is likewise displaced in the process from the blocking position thereof according to FIG. 5a in the injection direction R. The actuating plunger 24, which is still in contact via the side arm 80 thereof with the pivot arm 88 is moved along with the pivot arm 88 as a result of the action of the spring 78, and therefore moves into the stop position on the injection plunger 12 according to FIG. 5b. Up to this moment the snap-in hook 84 continues to be held in the released position by the pivot arm 88. However, as soon as the actuating plunger 24 can no longer continue to move along with the pivot arm 88 in the injection direction in the same manner because of the resistance by the injection plunger 12, the snap-in hook 84 is pivoted due to the spring 86 against the injection slide 20.

FIG. 5c shows the contact mechanism 70 with the cover 14 fully closed (according to FIG. 5d). As can be seen from this figure, the first member 90 is displaced in this position so far into the injection direction R against the bias spring FV that the pivot arm 88 is pivoted laterally into a release position and, as a result, completely unblocks the movement of both the side arm 80 and the snap-in hook 84. This causes the snap-in hook 84, as a result of the action of the spring 86, to be pivoted into a blocking position in which the actuating plunger 24 is fixed in place in a form-closed manner on the injection slide 20.

FIG. 5c therefore shows the injection device 2 in the stop position of the actuating device 18 with the actuating stop 26 fixed in place with respect to the injection slide 20, this stop position being detected by a sensor 94, which is provided on the actuating stop 26 by way of example, and being signaled to the injection volume adjustment 28 (see FIG. 5d). As an alternative thereto, it would be possible to provide a sensor that merely detects the closed state of the cover 14 and signals same to the injection volume adjustment 28 (not shown).

In both cases, the injection volume adjustment 28 is implemented in the form of an electronic component of the control unit 54 of the motor 52 (see FIG. 4), on which a desired injection volume of the medication M to be injected can be set for example by means of an input/display unit E/A (see FIG. 3) provided on the housing 4.

The injection volume adjustment 28 is additionally connected to a position sensor 95 (see FIG. 5c) that detects the position setting of the pricking depth stop 64 and communicates same to the injection volume adjustment 28. The position sensor 95 can be formed for example by a slide potentiometer for this purpose.

On the basis of the information signaled by the sensors 94, 95 and the desired injection volume set, the injection volume adjustment 28 determines, starting from the stop position, a pricking distance wE that is predefined by the position of the pricking depth stop 64 and an injection distance wl that is dependent upon the set injection volume for performing the injection stroke, according to the dot-and-dash illustration in FIG. 5d. In the process, a total stroke distance wG is obtained for the injection slide 20 starting from the stop position, which total stroke distance is now limited by the transport mechanism 50 in such a way that same is displaced—as outlined by the dash-and-dot line—into a corresponding position via a counting function of the injection volume adjustment 28 with regard to a completed number of revolutions of the motor 52.

Starting from the position shown in FIG. 5d, the injection device 2 upon actuation of the start button 60 then first performs the pricking stroke. During the pricking stroke the pricking slide 16 is displaced together with the injection slide 20 by means of the compression spring 48 along the pricking distance wE and the needle 62 emerges from the housing 4, as shown by dot-and-dash lines. The pricking stroke ends by the pricking slide 16 making contact with the pricking depth stop 64 (see dot-and-dash line in FIG. 5c).

After that, only the injection slide 20 continues to be displaced along the injection distance wl by the compression spring 48. As soon as the injection slide 20 comes to a stop, as shown by the dot-and-dash line in FIG. 5d, against the transport mechanism 50 that functions as the end stop, the amount of medication M predefined via the injection volume adjustment 28 is expressed from the injection mechanism 8 and the injection stroke is therefore complete. After that, the retention time and the return stroke can then be performed corresponding to the embodiment according to FIGS. 1 and 2.

Alternatively to the embodiment of the injection volume adjustment 28 as an electronic component of the control unit 54 according to FIG. 4, same may alternatively also be implemented as a mechanical unit. For example, a stop that ends the injection stroke could be provided for this purpose between the injection slide and the pricking slide (not shown).

What is claimed is:

1. An injection device (2) comprising:
a housing (4) in which a receiving chamber (6) is provided for an injection mechanism (8) to be inserted having an injection fluid container (10) that can be expressed by means of an injection plunger (12), and
an actuating device (18) that can be driven for automatically expressing the injection fluid container (10), said actuating device being capable of being displaced between
an insertion or removal position outside the receiving chamber and an injection position within the receiving chamber (6),
wherein the actuating device (18) is spaced by a release distance (d) from the receiving chamber (6) in the insertion or removal position,
wherein said injection device further comprises a contact mechanism (22, 70) by means of which the actuating device (18), can be brought into a stop position that is free of play and in which an actuating stop (26) of the actuating device (18) which is held movable on the actuating device (18) contacts the injection plunger (12) and the contact mechanism (22) has fixing means whereby the actuating stop (26) can be fixed in place on the actuating device (18) according to the position of the injection plunger (12),
and whereby in the stop position at the same time an injection volume adjustment (28) is automatically actuated to define a zero position for the injection volume adjustment
wherein the injection volume adjustment (28) can be actuated via the contact mechanism (22, 70), and
wherein said injection device further comprises an actuating plunger (24) carrying the actuating stop (26), the actuating plunger (24) being displaceable on the actuating device (18) in the injection direction (R), and the fixing means on contact of the actuating stop (26) with the injection plunger (12) create a form closure that acts opposite to the injection direction (R).

2. The injection device according to claim 1, characterized in that the injection volume adjustment (28) limits, starting from the stop position, a stroke distance (wH; wG) of the actuating device (18) along an injection direction (R).

3. The injection device according to claim 1, characterized in that the contact mechanism (70) can be activated according to a position of a cover (14) of the housing (4).

4. The injection device according to claim 3, characterized in that the contact mechanism (70) has an actuating member capable of being displaced through the cover (14) that assumes a blocking position when the cover is open (14) in which it holds the fixing means and the actuating plunger (24)

against a respective bias in the insertion or removal position in which the actuating plunger (24) is arranged in a rear stop position and the fixing means are released.

5. The injection device according to claim 4, characterized in that the actuating member is held on a direction change gear unit (76) that is biased into the insertion or removal position, and the cover (14) when closed presses the actuating member via the direction change gear unit (76) against a spring force (FV) into a release position in which it is spaced apart both from the actuating plunger (24) and from the locking device.

6. The injection device according to claim 1, characterized in that the contact mechanism (22, 70) has a coupling element (40) capable of being displaced transverse to the injection direction (R), which is capable of being displaced into an end position on contact of the actuating stop (26) with the injection plunger (12) in which end position it fixes the actuating plunger (24) in place both with respect to the actuating device (18) and on a movable stop element (36) of the injection volume adjustment (28).

7. The injection device according to claim 6, characterized in that the movable stop element (36) has a toothing (38) with which a mating toothing (42) of the coupling element (40) can be brought into engagement.

8. The injection device according to claim 6, characterized in that the injection volume adjustment (28) has an adjustable end stop (30) that is arranged in the movement direction of the movable stop element (36).

9. The injection device according to claim 8, characterized in that the end stop (30) is displaceable via a set screw (32) that is accessible from outside the housing (4).

10. The injection device according to claim 1, characterized in that the injection volume adjustment (28) is formed by a control unit (54) of an electric motor (52) that is capable of being actuated by a sensor (94) with which the stop position of the actuating device (18) can be detected.

11. The injection device according to claim 10, characterized in that the injection volume adjustment (28) has a counting function whereby a number of completed revolutions of the motor (52) starting from the stop position can be set.

\* \* \* \* \*